United States Patent
Wang et al.

(10) Patent No.: US 10,492,518 B2
(45) Date of Patent: Dec. 3, 2019

(54) BLOOD LIPID-LOWERING COMPOSITION, METHOD FOR PREPARING THE SAME AND USE THEREOF

(71) Applicant: INFINITUS (CHINA) COMPANY LTD., Jiangmen, Guangdong (CN)

(72) Inventors: Lei Wang, Guangdong (CN); Hongwei Zhao, Guangdong (CN); Qingtao Tang, Guangdong (CN)

(73) Assignee: INFINITUS (CHINA) COMPANY LTD., Jiangmen, Guangdong (CN)

( * ) Notice: Subject to any disclaimer, the term of this patent is extended or adjusted under 35 U.S.C. 154(b) by 0 days.

(21) Appl. No.: 16/217,030

(22) Filed: Dec. 11, 2018

(65) Prior Publication Data

US 2019/0307158 A1 Oct. 10, 2019

(30) Foreign Application Priority Data

Apr. 9, 2018 (CN) .......................... 2018 1 0311275

(51) Int. Cl.

| | |
|---|---|
| *A61K 36/30* | (2006.01) |
| *A23L 33/105* | (2016.01) |
| *A61K 36/31* | (2006.01) |
| *A61K 36/286* | (2006.01) |
| *A61K 9/48* | (2006.01) |
| *A61P 3/06* | (2006.01) |
| *A23L 33/21* | (2016.01) |

(52) U.S. Cl.
CPC ............ *A23L 33/105* (2016.08); *A23L 33/21* (2016.08); *A61K 9/4858* (2013.01); *A61K 9/4866* (2013.01); *A61K 36/286* (2013.01); *A61K 36/30* (2013.01); *A61K 36/31* (2013.01); *A61P 3/06* (2018.01); *A23V 2002/00* (2013.01); *A23V 2200/30* (2013.01); *A23V 2250/21* (2013.01); *A23V 2250/5036* (2013.01); *A23V 2250/5118* (2013.01); *A23V 2250/6406* (2013.01); *A23V 2300/31* (2013.01); *A61K 2236/15* (2013.01)

(58) Field of Classification Search
None
See application file for complete search history.

(56) References Cited

U.S. PATENT DOCUMENTS

| | | | | |
|---|---|---|---|---|
| 6,667,064 | B2 * | 12/2003 | Surette | A61K 31/201 424/725 |
| 7,959,950 | B2 * | 6/2011 | Evans | A23L 33/115 424/489 |
| 8,623,433 | B1 * | 1/2014 | Maru | A23L 2/44 424/764 |

FOREIGN PATENT DOCUMENTS

RU 2246964 C1 * 2/2005

OTHER PUBLICATIONS

Polyunsaturated fatty acids in the food chain in the United States, Am J Clin Nutr 2000;71(suppl):179S-88S.

* cited by examiner

*Primary Examiner* — Susan Hoffman

(74) *Attorney, Agent, or Firm* — Yue(Robert) Xu; Apex Attorneys at Law, LLP

(57) ABSTRACT

The present disclosure relates to the field of food and/or drug technology. Disclosed is a blood lipid-lowering composition, method for preparing the same and use thereof. The blood lipid-lowering composition comprises echium seed oil, camelina seed oil and safflower seed oil. The specific natural substances echium seed oil, camelina seed oil and safflower seed oil are used as the functional ingredients to form a natural composition that can significantly reduce the total cholesterol and triglyceride levels and increase the content of the serum apolipoprotein A1, having an obvious blood lipid-lowering function, which may be used in developing and preparing blood lipid-lowering drugs and foods, especially health care foods.

3 Claims, 1 Drawing Sheet

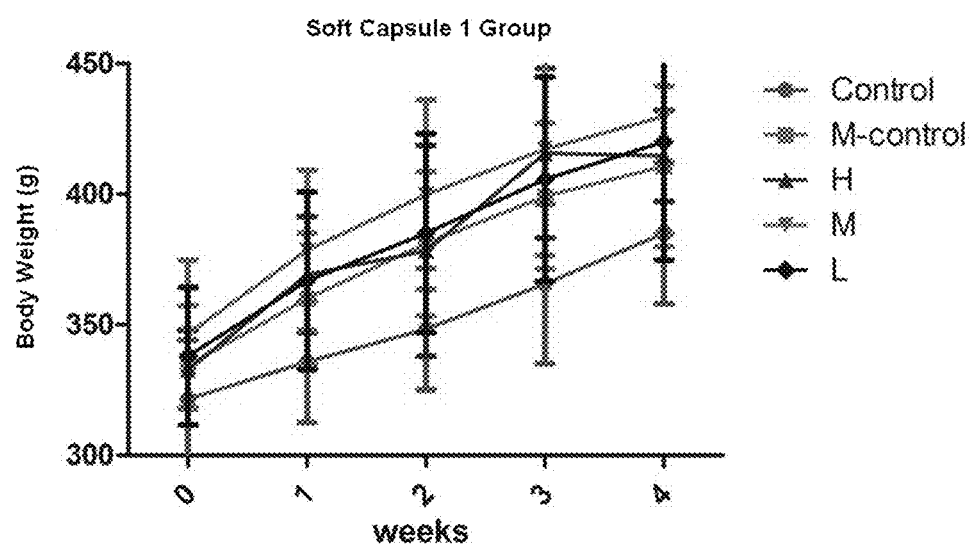

BLOOD LIPID-LOWERING COMPOSITION, METHOD FOR PREPARING THE SAME AND USE THEREOF

CROSS REFERENCE TO RELATED APPLICATIONS

This application claims the priority of Chinese Patent Application No. 201810311275.5, filed on Apr. 9, 2018, and the disclosures of which are hereby incorporated by reference.

FIELD

The present disclosure relates to the field of food and/or drug technology, specifically to a blood lipid-lowering composition, method for preparing the same and use thereof.

BACKGROUND

"Cardiac vessel" is the life river of human body. However, for decades, the diet of modern people has gradually become exquisite from simple and natural. In addition, since the beginning of the industrial society, busy work and life make most office workers and laborers rely on "dining out", and efficiency requirement easily replaces the consideration of health. As a result, blood lipid in the body becomes abnormal with this change. The "riverbed" of the blood vessels inside our body also undergoes a severe test. With the "hoarding" of fat in the blood, the blood vessel riverbed is "reluctantly" raised, and hyperlipidemia is also formed.

Hyperlipidemia is a "rich people's disease" derived from modern society, which is the source of many diseases. It is called "silent killer", and its damages to the body are hidden, gradual, progressive and systemic. One of the direct damages is accelerating systemic atherosclerosis, which is the main reason causing cardiovascular and cerebrovascular disease. Hyperlipidemia also leads to fatty liver, liver cirrhosis, cholelithiasis, pancreatitis, retinal hemorrhage, blindness, peripheral vascular disease, claudication, hyperuricemia and so on.

People's living standard has increased significantly in recent years, and consumption concept and health concept of people have changed a lot. In order to avoid the adverse effects of being unhealthy, people pay more and more attention to the use of nutraceuticals. Currently, the health care foods for improving hypertension, hyperglycemia and hyperlipidemia are in the form of oral liquid, tablet and animal glue soft capsule. However, oral liquid has disadvantages of inconvenience of carrying, poor stability and short storage time. Large doses of excipients such as starch and hydroxymethyl cellulose are often added to the tablet when the tablets are made, which causes a long disintegration time. The animal glue soft capsule has a long disintegration time. Also, for no matter which kind of the products, the choice of functional ingredient is not perfect.

SUMMARY

In view of the above, an object of the present disclosure is to provide a blood lipid-lowering composition, which has an excellent blood lipid-lowering efficacy.

Another object of the present disclosure is to provide use of the above composition in drugs and/or foods, especially health care foods.

In order to realize the above objects, the present disclosure provides the following technical solution.

A blood lipid-lowering composition, comprising echium seed oil, camelina seed oil and safflower seed oil, preferably, consisting of echium seed oil, camelina seed oil and safflower seed oil.

In the present disclosure, echium seed oil, camelina seed oil and safflower seed oil are from natural plants echium, camelina and safflower, which are used as active ingredients to form a natural composition having an obvious blood lipid-lowering function. As preferred, the mass ratio of echium seed oil, camelina seed oil and safflower seed oil is (95 to 60):(40 to 6):(20 to 2).

In the embodiments of the present disclosure, the mass ratio of echium seed oil, camelina seed oil and safflower seed oil is 9:1:1, 8:2:1, 8:1:1 or 7:3:1.

The present disclosure references the test method of adjunctive blood lipid-lowering function in the *Technical specification for health care food inspection and evaluation* (2012 Updated Edition), and efficacy tests are performed on the composition of the present disclosure. The results show that, compared with the model control group, the serum total cholesterol and triglyceride levels decrease in each dosage group of the composition, and all the differences are significant. At the same time, the serum HDL-cholesterol level in the composition group is higher than that of the model control group. The results indicate that the composition of the present disclosure has a function of reducing the total cholesterol and triglyceride, and the effect is better than the positive control groups, fish oil and atorvastatin calcium on the market.

In addition, the composition significantly increases the content of serum apolipoprotein A1 in SD rat, and the effect is better than the fish oil and atorvastatin calcium of the positive control groups. Apo-A1 protein is the main high-density lipoproteins, and it involves in the formation of the HDL particles; it is also the activator of the lecithin-cholesterol acyltransferase, and plays a major role in the reverse cholesterol transport. It can be concluded from the results that the composition of the present disclosure inhibits the formation of hyperlipidemia through adjusting the content of serum Apo-A1.

Based on the test results above, the present disclosure provides use of the blood lipid-lowering composition for the preparation of blood lipid-lowering drugs and/or foods, particularly health care foods. Therein, the food is preferably a health care food such as a health care food in the form of a soft capsule, an oral liquid, a tablet and so on.

In a specific use, the present disclosure provides a blood lipid-lowering soft capsule, which comprises the blood lipid-lowering composition of the present disclosure, and other substances that do not affect the efficacy of the blood lipid-lowering composition can also be added.

The soft capsule of the present disclosure are preferably prepared by coating the content with a vegetable gum, wherein the vegetable gum comprises Carrageenan, hydroxypropyl starch, glycerol and water. Each of the raw materials of the soft capsule is sourced from plant, and has a broad suitable population. At the same time, the disintegration time of this soft capsule is shorter than that of the gelatin soft capsule, which makes it more suitable to be used in preparing the soft capsule of the blood lipid-lowering composition of the present disclosure.

In addition, the present disclosure further provides a method for preparing the blood lipid-lowering composition, comprising: subjecting echium seed, camelina seed and safflower seed respectively to pulverization and pressing to prepare oils, filtering to obtain echium seed oil, camelina seed oil and safflower seed oil, and mixing the oils to obtain the blood lipid-lowering composition. Except for the above preparation method, it is also possible to directly mix echium seed oil, camelina seed oil and safflower seed oil purchased from the market.

The above mixed blood lipid-lowering composition is filtered and filled with an antioxidant gas for storage, and soft capsules can be prepared by soft capsule technology.

It can be concluded from the above technical solution that the present disclosure uses specific natural substances echium seed oil, camelina seed oil and safflower seed oil as the functional ingredient to prepare a natural composition that can significantly reduce the total cholesterol and triglyceride levels and increase the content of the serum apolipoprotein A1, having an obvious blood lipid-lowering function, which may be used in developing and preparing blood lipid-lowering drugs and foods, especially health care foods.

BRIEF DESCRIPTION OF DRAWINGS

FIG. 1 is a line graph that shows the effect of the composition of the present disclosure on the body weight of SD rat; wherein, "Control" is the blank control group, "M-control" is the model control group, H, M and L are successively three groups of the high, middle and low dosage of the composition of the present disclosure.

DETAILED DESCRIPTION

The present disclosure provides a blood lipid-lowering composition, the method for preparing the same and use thereof. One of ordinary skill in the art can learn from the contents herein and improve the process parameters appropriately. In particular, it shall be noted that all the similar substitutions and modifications are apparent to one of ordinary skill in the art and are to be considered within the scope of the present disclosure. The composition and the method for preparing the same and the application thereof of the present disclosure have been described with examples. It is apparent that one of the ordinary skill in the art can make change or modify the combination to the composition and the method for preparing the same and the application thereof of the present disclosure without departing from the spirit, scope and spirit of the disclosure, therefore realizing and applying the techniques of the present disclosure.

Unless otherwise specified, each of the test raw materials used in the specific examples of the present disclosure are from the same source and with the same quality. The conditions of the tests are consistent except for the required differences.

A blood lipid-lowering composition provided by the present disclosure, the method for preparing the same and the application thereof will be further illustrated hereinafter.

Example 1: Composition of the Present Disclosure
405 mg of echium seed oil, 45 mg of camelina seed oil and 45 mg of safflower seed oil.

Example 2: Composition of the Present Disclosure
400 mg of echium seed oil, 50 mg of camelina seed oil and 50 mg of safflower seed oil.

Example 3: Composition of the Present Disclosure
360 mg of echium seed oil, 90 mg of camelina seed oil and 45 mg of safflower seed oil.

Example 4: Composition of the Present Disclosure
315 mg of echium seed oil, 135 mg of camelina seed oil and 45 mg of safflower seed oil.

Example 5: Test of the Blood Lipid-Lowering Efficacy
Experiment object: compositions of examples 1 to 4, single component group (500 mg of echium seed oil), and two positive control groups: fish oil group (180 mg of EPA and 120 mg of DHA in each 1000 mg oil fish, purchased from Amway), and atorvastatin calcium group (each tablet was 20 mg containing 10 mg of active ingredient atorvastatin calcium, purchased from Pfizer Pharmaceutical Co., Ltd.).

Reference was made to the test method of adjunctive blood lipid-lowering function in the *Technical specification for health care food inspection and evaluation*. The SPF grade male SD rats were chosen as the experimental animals. After the adaptation period, an animal model of mixed hyperlipidemia was established, and the rats were randomly divided into groups according to the TC level.

There were three dosage groups, two positive control groups, one blank control group and one model control group. In low-dosage group, the dosage of the test sample was equal to 5 times (166.77 mg/kg) of the recommended amount for human; for the other two dosage groups, the dosages were respectively equal to 10 times (333.33 mg/kg) and 25 times (833.33 mg/kg) of the recommended amount for human. The dosage of the positive control group was equal to 5 times of the recommended amount for human (fish oil: 150 mg/Kg; atorvastatin calcium 0.83 mg/Kg). The blank control group and the model control group were administered with distilled water of the same volume by intragastric gavage. Each of the groups was weighed regularly. 30 days after the administration, blood samples were collected from the rats without fasting, and the serums were separated. TC (total cholesterol), TG (total triglyceride), (high-density lipoprotein cholesterol) and apo-A1 (apolipoprotein A1) were tested. The methods were illustrated in details hereinafter.

1. Adaptation Period
Adaptation period: in a barrier system the rats were fed for regular feed and observed for 5 to 7 days.

2. Model Establishment
The rats were randomly divided into 22 groups according to the weight, 6 rats per group. One group of rats was fed with regular feed as the blank control group. The other 21 groups were fed with high fat diet as the model control group. All rats were weighed once a week.

20 days after the model control groups were fed with high fat diet, blood samples (1 to 1.5 mL of blood from the tail vein) were collected from the rats of the blank control group and the model control group without fasting. After the blood collection, the serum were quickly separated and transferred to a new centrifuge tube, and then cryopreserved at −20° C. for test. ELISA test kits for cholesterol, triglyceride, HDL-cholesterol and LDL-cholesterol were used to test the levels of TC, TG, LDL-C and HDL-C in the rat serum. According to the TC level and the number of the test samples, the rats of the model control group were randomly divided into one model group, one fish oil control group, one atorvastatin calcium control group, and 6 test sample groups. Each test sample has 3 dosage groups.

3. Administration of the test sample: after grouping, the three dosage groups were orally administered with the test samples, and the two positive control groups were orally administered with fish oil test sample diluent and atorvastatin calcium diluent, and the blank control group and the model control group were administered with distilled water of the same volume daily. The blank control group was continuously fed with regular feed and the positive control group, the model control group and the three dosage groups were continuously fed with high fat diets. The rats were regularly weighed. At the end of the experiment, blood samples were collected form the eyeballs of the rats without fasting, and the serum were separated as soon as possible for the tests of TC, TG, HDL-C and apo-A1 levels in the serum.

4. Data Processing and Result Determination

The program for variance analysis was installed first, and the homogeneity test of variance was performed. If the variance is equal, the F value was calculated. When the F value<$F_{0.05}$, the differences between each group were not significant. When the F value≥$F_{0.05}$, and P≤$0.05$, statistics were performed by a pairwise comparison method between multiple experimental groups and one control group. Appropriate variable conversion was performed on non-normal or variance data. After the data met the requirement of normality or homogeneity of variance, statistic was performed on the converted data. If the converted data still could not achieve normality or homogeneity, the statistic was carried out by method of rank sum test.

5. Evaluation

Reference was made to *Technical specification for health care food inspection and evaluation* (2012 Updated Edition), and the determination of blood lipid-lowering function was performed according to the following standard: comparing the model control group with the blank control group, if the serum triglyceride increases, serum total cholesterol or LDL-cholesterol increases, and the differences are significant, then the model is recognized as established.

(1) Comparing each dosage group with the model control group, if the serum total cholesterol or LDL-cholesterol of any dosage group reduces, the serum triglyceride of any dosage group reduces, and the differences are significant, meanwhile, the serum HDL-cholesterol of each dosage group is not lower than that of the model control group, then the blood lipid-lowering function of the test sample in animal experiment is recognized as positive.

(2) Comparing each dosage group with the model control group, if the serum total cholesterol or LDL-cholesterol of any dosage group reduces and the difference is significant, meanwhile, the serum triglyceride of each dosage group is not obviously higher than that of the model control group, and the serum HDL-cholesterol of each dosage group is not obviously lower than that of the model control group, then the blood lipid-lowering function of the test sample in animal experiment is recognized as positive.

(3) Comparing each dosage group with the model control group, if the serum triglyceride of any dosage group decreases and the difference is significant, meanwhile, the serum total cholesterol and LDL-cholesterol of each dosage group are not significantly higher than that of the model control group, and the serum HDL-cholesterol is not obviously lower than that of the model control group, then the blood lipid-lowering function of the test sample in animal experiment is recognized as positive.

6. Results (1) Establishment of the Mixed Hyperlipidemia Model in SD Rat

The TC content in the serum of the blank control group was 936.46 μmol/L, and 1148.96 μmol/L in the model control group, and the difference was significant comparing with the blank control group (P=0.004, <0.01). The TG content in the serum of the blank control group was 146.20 μmol/L, and 190.62 μmol/L in the model control group, and the difference was significant comparing with the blank control group (P=0.005, <0.01). The HDL-C content in the serum of the blank control group was 727.84 μmol/L, and 734.67 μmol/L in the model control group, and the difference was not significant comparing with the blank control group (P=0.902, >0.05). The LDL-C content in the serum of the blank control group was 810.07 μmol/L, and 947.36 μmol/L in the model control group, and the difference was significant comparing with the blank control group (P=0.013, <0.05). When comparing the model control group with the blank control group, the serum TG, TC, LDL-C levels increased and the differences were significant, indicating that the mixed hyperlipidemia model in SD rat was established successfully.

(2) Effect on Body Weight of the SD Rats

FIG. 1 showed that the body weight growth rates of the groups with high fat diet (dosage groups and model control groups) of Example 1 were obviously faster than that of the blank control group with regular diet, but there was no significant difference between the weight of the dosage groups and the model control group. These results demonstrated that the composition of the present disclosure does not have obvious effect on the body weight of the SD rats.

(3) Effect on the Serum Total Cholesterol (TC) of the SD Rats

TABLE 1

| Group | Mean Value ± Standard Deviation (μmol/L) |
|---|---|
| M-control | 1148.96 ± 107.94 |
| Control | 936.47 ± 30.67** |
| Fish Oil | 1209.43 ± 105.23 |
| Atorvastatin Calcium | 1117.14 ± 171.07 |
| Example 1 H | 977.98 ± 88.03# |
| Example 1 M | 1053.19 ± 144.85 |
| Example 1 L | 1077.21 ± 108.55 |
| Example 2 H | 966.57 ± 39.45## |
| Example 2 M | 1051.72 ± 59.63# |
| Example 2 L | 1076.76 ± 135.44 |

Comment: * means comparing the blank group with the model group, wherein **means P < 0.01 and * means P < 0.05; #means comparing the dosage groups with the model group, and ##means P < 0.01 and #means P < 0.05.?

The results of the Table 1 show that the TC content in the serum of the high dosage group of the composition of Example 1 was 977.98 μmol/L; comparing with the model control group (1148.96 μmol/L), there was a significant difference (P<0.05). TC contents in the serum of the middle and low dosage groups were respectively 1053.20 μmol/and 1077.21 μmol/L, and there was no significant difference (P>0.05) comparing with the model control group. TC contents in the serum of the high and middle dosage groups of the composition of Example 2 were respectively 966.57 μmol/L and 1051.72 μmol/L; comparing with the model control group (1148.96 μmol/L), there were significant differences (P<0.01, and P<0.05). TC content in the serum of the low dosage groups was 1076.76 μmol/L, and there was no significant difference (P>0.05) comparing with the model control group. At the same time, there was no significant difference between the two positive control groups and the model control group. The results of these experiments demonstrated that the composition of Example 1 of the present disclosure significantly reduced the TC content in the serum of the SD rats, and the effect was better than that of the fish oil and atorvastatin calcium.

(4) Effect on the Serum Triglyceride (TG) of the SD Rats

TABLE 2

| Group | Mean Value ± Standard Deviation (μmol/L) |
|---|---|
| M-control | 190.62 ± 24.59 |
| Control | 146.20 ± 14.73** |
| Fish Oil | 198.77 ± 31.65 |
| Atorvastatin Calcium | 189.71 ± 45.83 |
| Single Component Group H | 180.92 ± 32.77 |
| Single Component Group M | 179.32 ± 30.81 |

TABLE 2-continued

| Group | Mean Value ± Standard Deviation (μmol/L) |
|---|---|
| Single Component Group L | 187.50 ± 33.24 |
| Example 1 H | 159.03 ± 24.02# |
| Example 1 M | 155.19 ± 20.15# |
| Example 1 L | 176.96 ± 34.12 |
| Example 2 H | 151.02 ± 32.75# |
| Example 2 M | 175.07 ± 30.72 |
| Example 2 L | 178.86 ± 29.62 |
| Example 3 H | 154.94 ± 27.61# |
| Example 3 M | 195.95 ± 31.31 |
| Example 3 L | 208.60 ± 38.47 |
| Example 4 H | 151.03 ± 32.753# |
| Example 4 M | 175.06 ± 30.73 |
| Example 4 L | 178.87 ± 29.60 |

Comment: * means comparing the blank group with the model group, wherein **means $P < 0.01$ and * means $P < 0.05$; #means comparing the dosage groups with the model group, and ## means $P < 0.01$ and #means $P < 0.05$.?

The results of the Table 2 showed that the TG content in the serum of the high dosage group of the composition of Example 1 was 159.03 μmol/L, and there was a significant difference ($P<0.05$) comparing with the model control group (190.62 μmol/L). TG content in the serum of the middle dosage group was 155.19 μmol/L, and there was a significant difference ($P<0.05$) comparing with the model control group. TG content in the serum of the low dosage group was 176.96 μmol/L, and there was no significant difference ($P>0.05$) comparing with the model control group.

The TG content in the serum of the high dosage group of the composition of Example 2 was 151.01 μmol/L, and there was a significant difference ($P<0.05$) comparing with the model control group (190.62 μmol/L). TG contents in the serum of the middle and low dosage groups were respectively 175.07 μmol/L and 178.85 μmol/L, and there was no significant difference ($P>0.05$) comparing with the model control group.

The TG content in the serum of the high dosage group of the composition of Example 3 was 154.94 μmol/L, and there was a significant difference ($P<0.05$) comparing with the model control group (190.62 μmol/L). TG content in the serum of the high dosage group of the composition of Example 4 was 151.03 μmol/L, and there was a significant difference ($P<0.05$) comparing with the model control group (190.62 μmol/L).

The TG contents in the serum of the high, middle and low dosage groups of the single component group were 180.92 pmol/L, 179.32 μmol/L and 187.50 μmol/L, respectively, and there was no significant difference ($P>0.05$) comparing with the model control group (190.62 μmol/L).

There was also no significant difference between the two positive control groups and the model control group. The results of these experiments showed that the composition of the present disclosure significantly decreased the TG content in the serum of the SD rats, and the effect was better than that of the fish oil and atorvastatin calcium groups and the single component group.

(5) Effect on the Serum HDL-C of the SD Rats

TABLE 3

| Group | Mean Value ± Standard Deviation (μmol/L) |
|---|---|
| M-Control | 734.86 ± 40.59 |
| Control | 727.84 ± 123.11 |
| Fish Oil | 815.14 ± 230.24 |
| Atorvastatin Calcium | 919.74 ± 150.63# |

TABLE 3-continued

| Group | Mean Value ± Standard Deviation (μmol/L) |
|---|---|
| Single Component Group H | 874.57 ± 178.83 |
| Single Component Group M | 881.54 ± 215.03 |
| Single Component Group L | 887.16 ± 219.67 |
| Example 1 H | 895.00 ± 174.97# |
| Example 1 M | 997.48 ± 252.05## |
| Example 1 L | 839.52 ± 168.13 |
| Example 2 H | 876.72 ± 135.17 |
| Example 2 M | 895.46 ± 133.71# |
| Example 2 L | 881.95 ± 234.62 |
| Example 3 H | 849.22 ± 101.22 |
| Example 3 M | 853.91 ± 236.53 |
| Example 3 L | 861.75 ± 239.70 |
| Example 4 H | 898.88 ± 83.81# |
| Example 4 M | 973.12 ± 157.44## |
| Example 4 L | 760.37 ± 137.00 |

Comment: * means comparing the blank group with the model group, wherein ** means $P < 0.01$ and * means $P < 0.05$; #means comparing the dosage groups with the model group, and ##means $P < 0.01$ and #means $P < 0.05$.?

The results of the Table 3 showed that the HDL-C contents in the serum of the high, middle and low dosage groups of the composition of Example 1 were 895.00 μmol/L, 997.48 μmol/L and 839.52 μmol/L, respectively. Comparing with the model control group (734.86 μmol/L), the middle dosage group showed an extremely significant difference ($P<0.01$), and the high dosage group showed a significant difference ($P<0.05$).

Comparing with the model group, the HDL-C level in the serum of the three dosage groups of Example 2 increased. The HDL-C content in the serum of the high dosage group was 876.72 μmol/L, and there was no significant difference ($P>0.05$) comparing with the model control group (734.86 μmol/L). The HDL-C contents in the serum of the middle and low dosage groups were respectively 895.46 μmol/L and 881.95 μmol/L, and there was a significant difference ($P<0.05$) between middle dosage group and the model control group.

Comparing with the model group (734.86 μmol/L), the HDL-C level in the serum of the high, middle and low dosage groups of Example 3 did not show significant difference. The HDL-C contents in the serum of the high and middle dosage groups of Example 4 were respectively 898.88 μmol/L and 973.12 μmol/L, and there were significant differences ($P<0.05$, and $P<0.01$) comparing with the model control group. The results above indicated that the composition of the present disclosure significantly improved the HDL-C content in the serum of the SD rats.

The HDL-C contents in the serum of the high, middle and low dosages of the single component group were 874.57 μmol/L, 881.54 μmol/L and 887.16 μmol/L, respectively. Comparing with the model control group (734.86 μmol/L), the HDL-C level in the serum increased, but there was no significant difference.

In the positive control groups, only atorvastatin calcium group has a significant difference from the model group ($P<0.05$). Comparing with the single component group and the positive control groups, the composition of the present disclosure has a better effect than that of the two experimental groups.

(6) Effect on the Serum LDL-C of the SD Rats

TABLE 4

| Group | Mean Value ± Standard Deviation (μmol/L) |
|---|---|
| M-control | 947.36 ± 89.26 |
| Control | 810.07 ± 60.36 |

TABLE 4-continued

| Group | Mean Value ± Standard Deviation (μmol/L) |
|---|---|
| Fish Oil | 945.27 ± 139.98 |
| Atorvastatin Calcium | 853.24 ± 236.19 |
| Example 1 H | 907.27 ± 243.42 |
| Example 1 M | 920.78 ± 90.08 |
| Example 1 L | 983.71 ± 183.33 |
| Example 2 H | 810.92 ± 80.28# |
| Example 2 M | 868.11 ± 109.04 |
| Example 2 L | 807.88 ± 148.94 |

Comment: * means comparing the blank group with the model group, wherein ** means P < 0.01 and * means P < 0.05; #means comparing the dosage groups with the model group, and ## means P < 0.01 and #means P < 0.05.?

The results of the Table 4 showed that the LDL-C contents in the serum of the high, middle and low dosage groups of Example 1 decreased comparing with the model group, but there was no significant difference.

The LDL-C content in the serum of the high dosage group of Example 2 was 810.92 μmol/L, and there was a significant difference (P<0.05) comparing with the model control group (947.36 μmol/L). The LDL-C contents in the serum of the middle and low dosage groups of Example 2 were 868.11 μmol/L and 807.88 μmol/L, and there was a significant difference (P<0.05) between the middle dosage group and the model control group.

Comparing the positive control group with the model group, there was no significant difference, especially the fish oil group, which was even equal to the model group, indicating that the composition of the present disclosure is superior to the positive control groups.

Effect on the Serum Apo-A1 of the SD Rats

TABLE 5

| Group | Mean Value ± Standard Deviation (μmol/L) |
|---|---|
| M-control | 2260.49 ± 201.25 |
| Control | 2271.27 ± 237.59 |
| Fish Oil | 2645.26 ± 626.25 |
| Atorvastatin Calcium | 2693.76 ± 435.48 |
| Single Component Group H | 3057.53 ± 389.92## |
| Single Component Group M | 2715.42 ± 324.11# |
| Single Component Group L | 2325.71 ± 540.44 |
| Example 1 H | 2609.00 ± 373.79 |
| Example 1 M | 2675.43 ± 496.39 |
| Example 1 L | 2933.80 ± 389.24## |
| Example 2 H | 2725.43 ± 357.92# |
| Example 2 M | 2545.46 ± 489.45 |
| Example 2 L | 2717.48 ± 401.72# |

Comment: * means comparing the blank group with the model group, wherein ** means P < 0.01 and * means P < 0.05; #means comparing the dosage groups with the model group, and ##means P < 0.01 and #means P < 0.05.?

Results of the Table 5 showed that the apo-A1 contents in the serum of high, middle and low dosage groups of the composition of Example 1 were 2609.00 μg/mL, 2675.43 μg/mL and 2933.80 μg/mL, respectively. Comparing with the model control group (2260.49 m/mL), the low dosage group showed an extremely significant difference (P<0.01).

The apo-A1 contents in the serum of the high, middle and low dosage groups of the composition of Example 2 were 2725.43 m/mL, 2545.46 μg/mL and 2717.48 μg/mL, respectively. Comparing with the model control group, the high and low dosage groups showed significant differences (P<0.05).

The apo-A1 contents in the serum of the high, middle and low dosage groups of the single component group were 3057.53 μg/mL, 2715.42 μg/mL and 2325.71 μg/mL, respectively. Comparing with the model control group, the high and middle dosage groups showed significant differences (P<0.01, and P<0.05).

There was no significant difference between the two positive control groups and the model control group. The results of these experiments showed that the composition of the present disclosure significantly increased the serum apo-A1 content of the SD rats, and the efficacy is superior to the fish oil and atorvastatin calcium.

Apo-A1 is the main HDL, which is related to the formation of HDL particles and also the main activator of LCAT (Lecithin-cholesterol acyltransferase). LCAT plays a key role in the reverse cholesterol transport, through which the non-lipidated cholesterol, which spreads and deposits in surrounding tissues, is catalyzed via the LCA to cholesterol, which is transferred to the liver by HDL, metabolized by the liver, and discharged to the gallbladder.

Example 6: Comparison of Disintegration Time of the Soft Capsules Made with Different Excipients The composition of Example 2 was chosen as the content of the soft capsules, and the contents were respectively packaged with the following excipients to prepare the soft capsules. Comparing the effect of different excipients on the disintegration time of the same content (mainly caused by the different types of excipients, the difference from the content ratio was not obvious):

Soft Capsule 1: Carrageenan, hydroxypropyl starch, glycerin, water;

Soft Capsule 2: gelatin, glycerin, water.

The contents of the two capsules were completely identical, and the same ingredients of the excipients were completely identical; the amount of Carrageenan+hydroxypropyl starch was equal to the amount of gelatin.

The instrument is generally equipped with 6 sets of measuring device in which the basket shaft is connected with the motor. Measuring method: before the measurement, the instrument device should be adjusted as necessary so that the bottom of the basket is 25 mm±2 mm from the inner bottom of the dissolution cup. The degassed dissolution medium were respectively measured and placed in each dissolution cups. The actual measured volume should not deviate from the specified volume by more than ±1%. After the temperature of the dissolution medium was constant at 37° C.±0.5° C., 6 test samples were respectively put into 6 dry baskets, and the baskets were dropped into the dissolution cups. Be careful that there should be no air bubble on the surface of the test samples. The instrument was started according to the speed specified under the categories, the disintegration of the capsule was observed, and the time when the capsule is completely disintegrated is recorded. The results were shown in the table below.

TABLE 6

| Name | Disintegration time after 0 month (min) | Disintegration time after accelerated 1 month (min) | Disintegration time after accelerated 2 months (min) | Disintegration time after accelerated 3 months (min) |
|---|---|---|---|---|
| Capsule 1 | 8 | 10 | 12 | 12 |
| Capsule 2 | 18 | 22 | 30 | 35 |

It can be obviously concluded from the results of the above table that the soft capsules prepared by the excipient components of the present disclosure has a shorter disintegration time, so that the soft capsules are easier to be disintegrated in the gastrointestinal tract.

The above are merely preferred embodiments of the present disclosure. It should be noted that a number of modifications and refinements may be made by one of ordinary skill in the art without departing from the principles of the present disclosure, and such modifications and refinements are also considered to be within the scope of the present disclosure.

What is claimed is:

1. A method of lowering blood lipid, comprising administering a blood lipid-lowering composition to a subject in need thereof, wherein the blood lipid-lowering composition comprises echium seed oil, camelina seed oil and safflower seed oil, wherein the mass ratio of echium seed oil, camelina seed oil and safflower seed oil is (95 to 60):(40 to 6):(20 to 2);

the composition is in the form of a soft capsule, and the soft capsule is prepared from a vegetable gum comprising Carrageenan, hydroxypropyl starch, glycerol and water.

2. The method according to claim 1, wherein the composition is a health care food.

3. The method according to claim 1, wherein the mass ratio of echium seed oil, camelina seed oil and safflower seed oil is 9:1:1, 8:2:1, 8:1:1 or 7:3:1.

* * * * *